(12) United States Patent
Abe

(10) Patent No.: US 10,853,450 B2
(45) Date of Patent: Dec. 1, 2020

(54) RADIOGRAPHING APPARATUS, RADIOGRAPHING SYSTEM, RADIOGRAPHING METHOD, AND PROGRAM

(71) Applicant: CANON KABUSHIKI KAISHA, Tokyo (JP)

(72) Inventor: Masahiro Abe, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 94 days.

(21) Appl. No.: 15/725,826

(22) Filed: Oct. 5, 2017

(65) Prior Publication Data

US 2018/0107788 A1 Apr. 19, 2018

(30) Foreign Application Priority Data

Oct. 17, 2016 (JP) ................................ 2016-203633

(51) Int. Cl.
| | | |
|---|---|---|
| *A61B 6/00* | (2006.01) | |
| *G06Q 50/22* | (2018.01) | |
| *G06F 19/00* | (2018.01) | |
| *G16H 40/63* | (2018.01) | |

(52) U.S. Cl.
CPC .......... *G06F 19/321* (2013.01); *A61B 6/4405* (2013.01); *A61B 6/465* (2013.01); *A61B 6/563* (2013.01); *G06Q 50/22* (2013.01); *G16H 40/63* (2018.01)

(58) Field of Classification Search
CPC ..... G06F 19/321; G16H 40/63; A61B 6/4405; A61B 6/465; A61B 6/563; G06Q 50/22

USPC ......................................................... 378/98
See application file for complete search history.

(56) References Cited

U.S. PATENT DOCUMENTS

| | | | |
|---|---|---|---|
| 2004/0086163 A1* | 5/2004 | Moriyama ........... | A61B 6/4494 382/131 |
| 2004/0086164 A1* | 5/2004 | Moriyama ............... | A61B 6/00 382/131 |
| 2004/0089710 A1* | 5/2004 | Moriyama ........... | A61B 6/4494 235/375 |
| 2005/0097220 A1* | 5/2005 | Koshiji ............... | G01N 23/223 709/238 |
| 2008/0025324 A1* | 1/2008 | Sawada ................. | H04L 41/00 370/400 |

(Continued)

FOREIGN PATENT DOCUMENTS

| | | |
|---|---|---|
| JP | 2001-144781 A | 5/2001 |
| JP | 2014-171520 A | 9/2014 |

(Continued)

*Primary Examiner* — Taeho Jo
(74) *Attorney, Agent, or Firm* — Canon U.S.A., Inc., IP Division

(57) ABSTRACT

A radiographing apparatus detects radiation to generate a radiographic image and includes a first communication unit that communicates with a communication device via a first communication method and a second communication unit that communicates with the communication device via a second communication method, wherein the first communication unit receives a communication request signal for requesting communication with the communication device via the second communication method, and wherein the second communication unit performs communication with the communication device via the second communication method based on the communication request signal.

14 Claims, 11 Drawing Sheets

(56) References Cited

U.S. PATENT DOCUMENTS

| | | | | |
|---|---|---|---|---|
| 2009/0011780 | A1* | 1/2009 | Salinas | H04L 51/28 455/466 |
| 2010/0104065 | A1* | 4/2010 | Eguchi | A61B 6/4233 378/62 |
| 2012/0286167 | A1* | 11/2012 | Eguchi | A61B 6/4494 250/393 |
| 2013/0088452 | A1* | 4/2013 | Glaser-Seidnitzer | A61B 6/548 345/173 |
| 2014/0152692 | A1* | 6/2014 | Masuda | G06F 19/3418 345/619 |
| 2014/0156306 | A1* | 6/2014 | Masuda | G06Q 10/10 705/3 |
| 2014/0156307 | A1* | 6/2014 | Masuda | G16H 30/20 705/3 |
| 2014/0188984 | A1* | 7/2014 | Kouda | H04L 67/10 709/203 |
| 2014/0254759 | A1* | 9/2014 | Haraguchi | H04N 5/32 378/62 |
| 2014/0292777 | A1* | 10/2014 | Kudo | A61B 6/461 345/520 |
| 2014/0295905 | A1* | 10/2014 | Koskinen | H04W 52/0206 455/522 |
| 2015/0078522 | A1* | 3/2015 | Makino | A61B 6/4405 378/62 |
| 2015/0078527 | A1* | 3/2015 | Iwamoto | A61B 6/4405 378/91 |
| 2015/0245456 | A1* | 8/2015 | Nishino | A61B 6/4411 378/62 |
| 2016/0029991 | A1* | 2/2016 | Tajima | A61B 6/461 378/98 |
| 2016/0048370 | A1* | 2/2016 | Zenoff | G09F 21/02 715/734 |
| 2016/0051216 | A1* | 2/2016 | Foos | A61B 6/5217 378/62 |
| 2016/0063203 | A1* | 3/2016 | Seo | G16H 10/60 705/3 |
| 2016/0112268 | A1* | 4/2016 | Chung | H04L 45/26 370/254 |
| 2016/0112434 | A1* | 4/2016 | Chung | H04W 4/08 726/4 |
| 2016/0174350 | A1* | 6/2016 | Tamura | A61B 6/563 378/114 |
| 2016/0228087 | A1* | 8/2016 | Oda | A61B 6/465 |
| 2016/0270746 | A1* | 9/2016 | Foos | G16H 40/63 |
| 2016/0345920 | A1* | 12/2016 | Tajima | A61B 6/5294 |
| 2016/0374640 | A1* | 12/2016 | Tamura | A61B 6/563 340/2.1 |
| 2018/0191728 | A1* | 7/2018 | Kim | H04L 63/126 |

FOREIGN PATENT DOCUMENTS

| | | |
|---|---|---|
| JP | 2015-83114 A | 4/2015 |
| JP | 2016-34470 A | 3/2016 |
| JP | 2016-101210 A | 6/2016 |

* cited by examiner

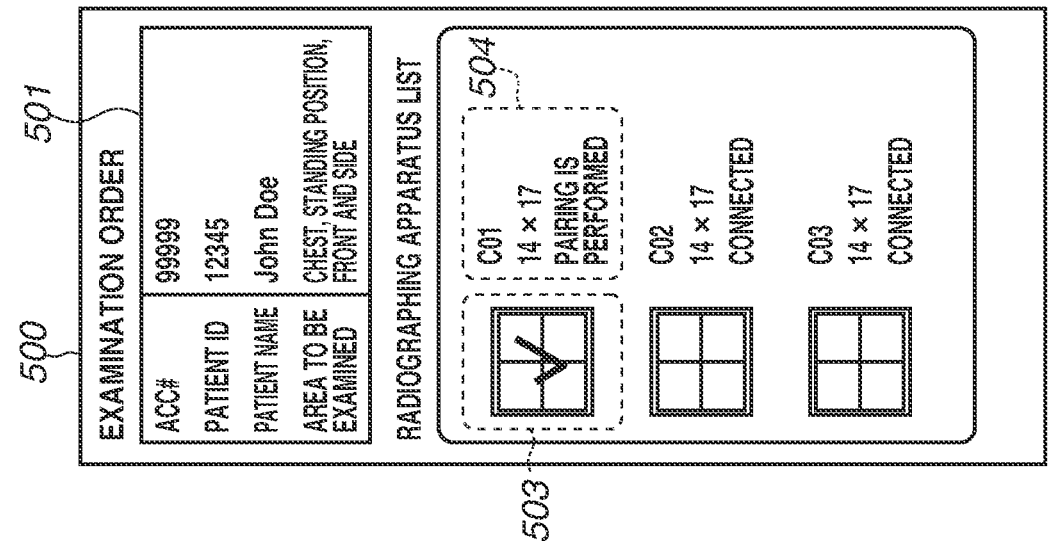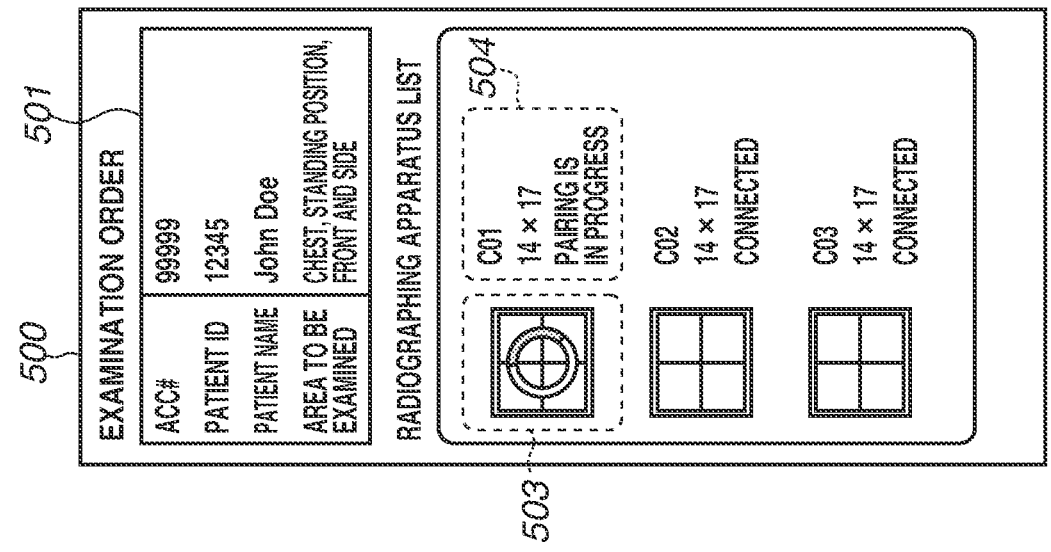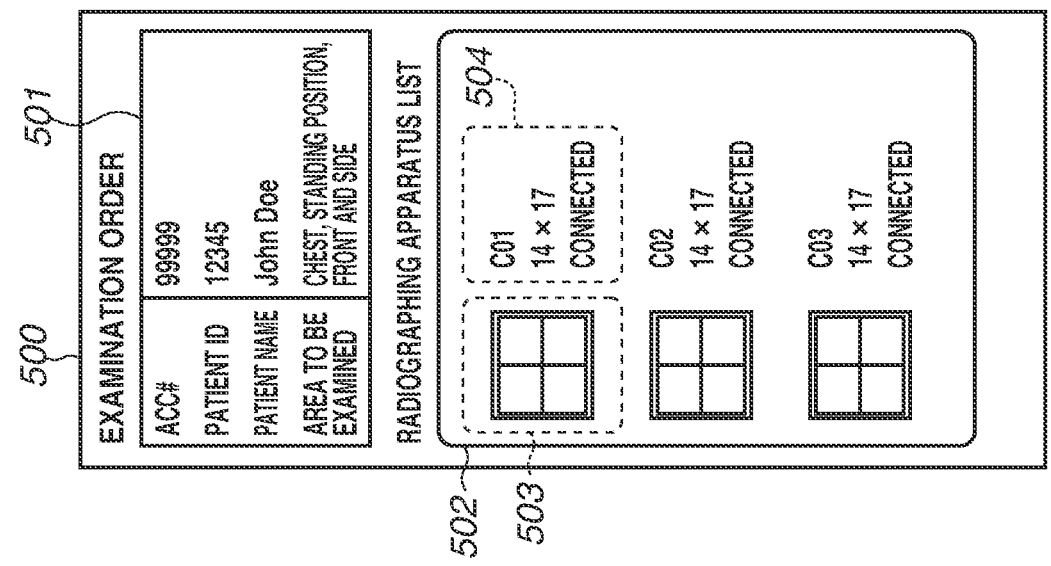

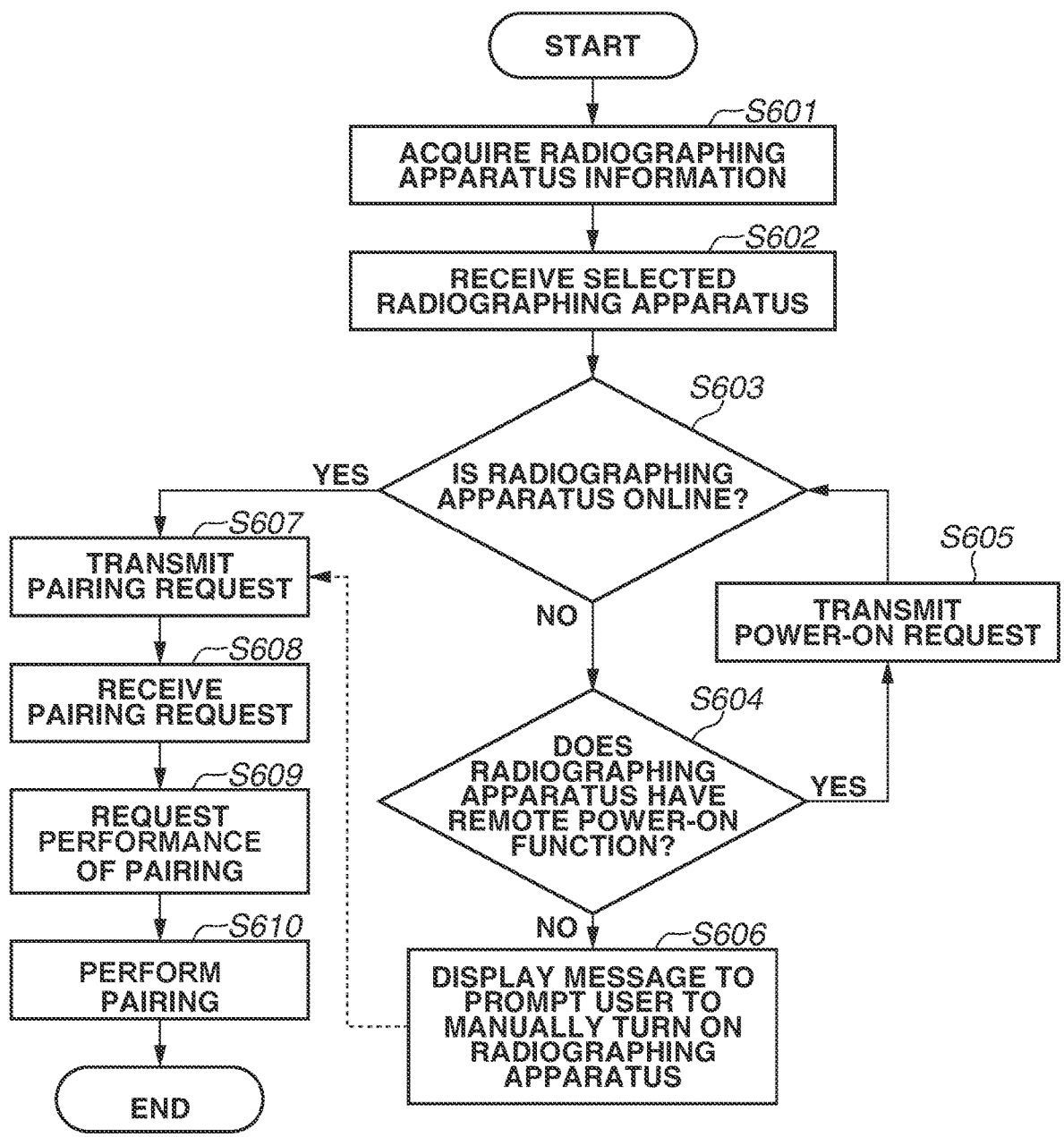

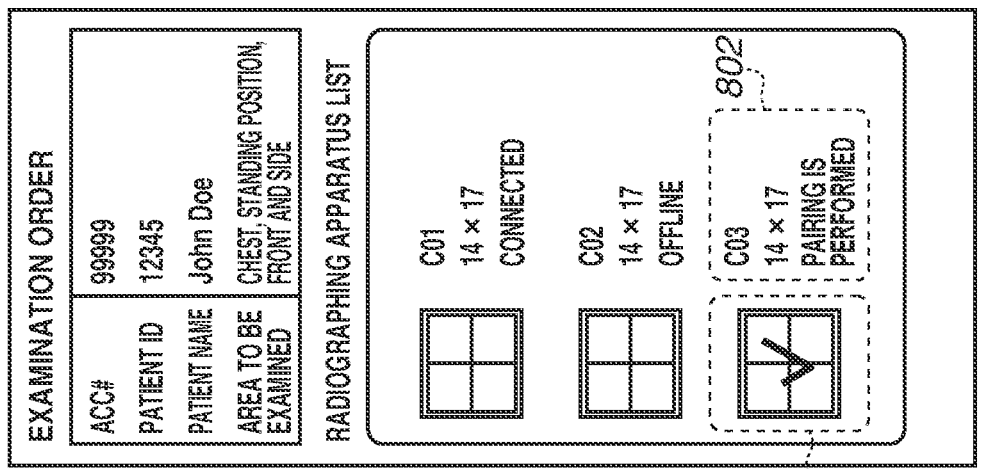
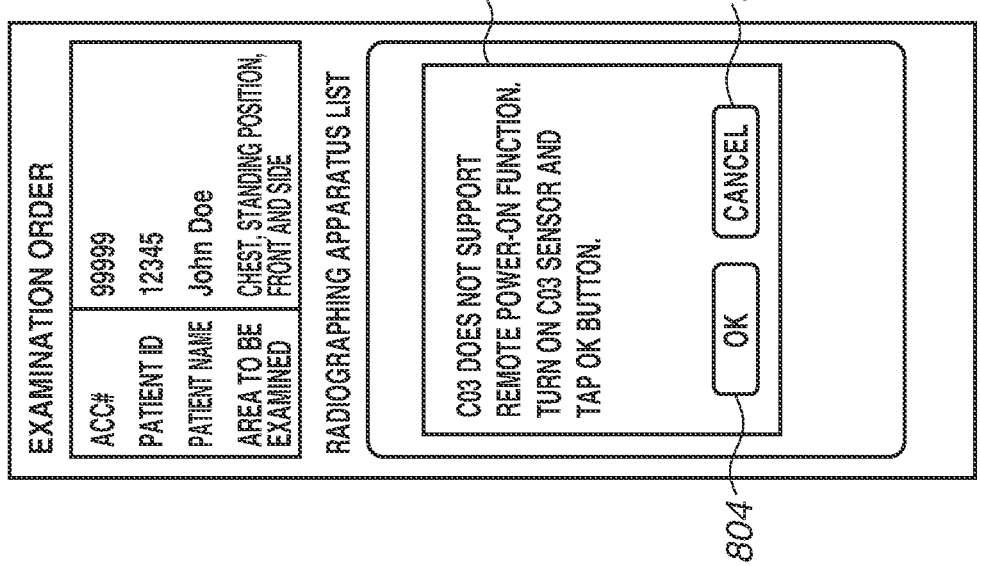
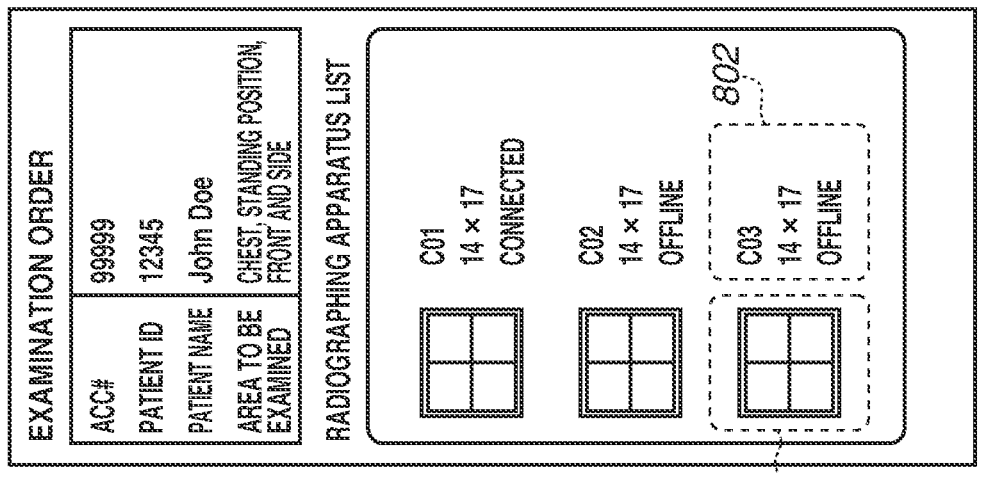

FIG.9A

| RADIOGRAPHING PROTOCOL | SENSOR SIZE |
|---|---|
| CHEST, FRONT AND SIDE | 14 × 17 |
| ABDOMEN, FRONT | 14 × 17 |
| HAND | 9 × 11 |
| KNEE JOINT | 11 × 14 |

FIG.9B

| RADIOGRAPHING APPARATUS NAME | SENSOR SIZE | PAIRING STATE |
|---|---|---|
| C01 | 14 × 17 | — |
| C02 | 14 × 17 | — |
| C03 | 14 × 17 | — |
| C04 | 11 × 14 | Tablet3 |
| C05 | 9 × 11 | — |
| C06 | 14 × 17 | Tablet2 |

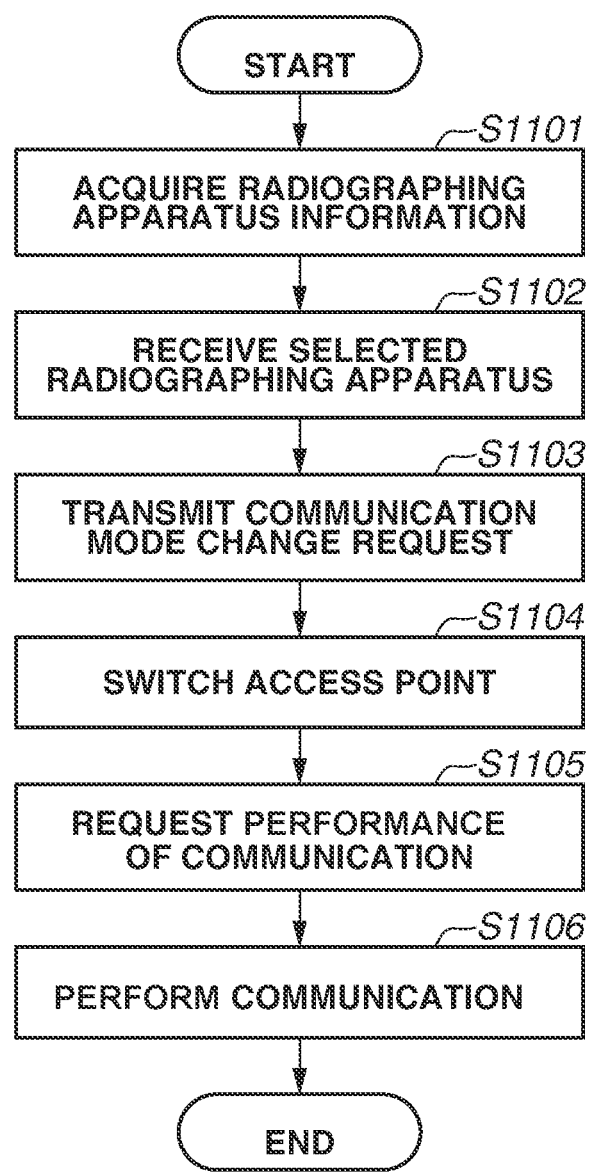

RADIOGRAPHING APPARATUS, RADIOGRAPHING SYSTEM, RADIOGRAPHING METHOD, AND PROGRAM

BACKGROUND

Field

The present disclosure relates to radiographing apparatuses, radiographing systems, radiographing methods, and programs.

Description of the Related Art

In recent years, bedside (round) radiographing operation has been increasingly conducted in hospitals. Specifically, a cart with a portable digital radiographing apparatus (sensor panel) placed thereon is brought into a patient's room to conduct radiographing on the patient in the room. Conventionally, the cart includes a console personal computer (PC) for controlling the sensor panel. In general, the console PC is a so-called clamshell note PC or a PC embedded in the cart.

Tablet-type mobile information terminals have been increasingly started to be used for general purposes. Having advantages in portability, activation speed, price, etc., tablet-type mobile information terminals have been introduced in the medical field, and round imaging systems using mobile information terminals have been discussed (refer to Japanese Patent Application Laid-Open Nos. 2016-34470 and 2016-101210).

To control radiographing using a mobile information terminal, the mobile information terminal needs to communicate with a radiographing apparatus. Many current mobile information terminals include a Bluetooth® communication interface, and communication between a mobile information terminal and a radiographing apparatus is performed using such a communication interface.

In the case of using Bluetooth®, a connection performing procedure called pairing needs to be executed to enable communications between devices.

In conventional pairing, two devices between which communication is not currently performed need to recognize each other, and this requires each device to be operated. Specifically, one of the devices is operated to shift to a pairing stand-by state, and the other device is operated to transmit a communication performance signal to the device in the pairing stand-by state so that a connection is performed.

As described above, since each device needs to be operated to perform communication between the devices, complicated operations can arise.

SUMMARY

According to at least one aspect of the present disclosure, a radiographing apparatus configured to detect radiation to generate a radiographic image includes a first communication unit that communicates with a communication device via a first communication method, and a second communication unit that communicates with the communication device via a second communication method, wherein the first communication unit receives a communication request signal for requesting communication with the communication device via the second communication method, and wherein the second communication unit performs communication with the communication device via the second communication method based on the communication request signal.

Further features will become apparent from the following description of exemplary embodiments with reference to the attached drawings.

BRIEF DESCRIPTION OF THE DRAWINGS

FIGS. 5A, 5B, and 5C illustrate an example of a graphical user interface (GUI) according to the first exemplary embodiment.

FIG. 6 is a flow chart according to a second exemplary embodiment.

FIGS. 8A, 8B, and 8C illustrate an example of a manual power-on GUI according to the second exemplary embodiment.

FIG. 9A illustrates an example of a correspondence table which specifies correspondences between sensor sizes and radiographing protocols according to a third exemplary embodiment. FIG. 9B illustrates an example of a correspondence table that specifies correspondences between sensor sizes and pairing states according to the third exemplary embodiment.

FIG. 11 is a flow chart according to the fourth exemplary embodiment.

DESCRIPTION OF THE EMBODIMENTS

A first exemplary embodiment will be described below with reference to the drawings. Exemplary embodiments described below are not intended to limit the scope of the claims. Not every combination of features described in the exemplary embodiments described below is always essential to a technical solution of the present disclosure.

Figure 1:
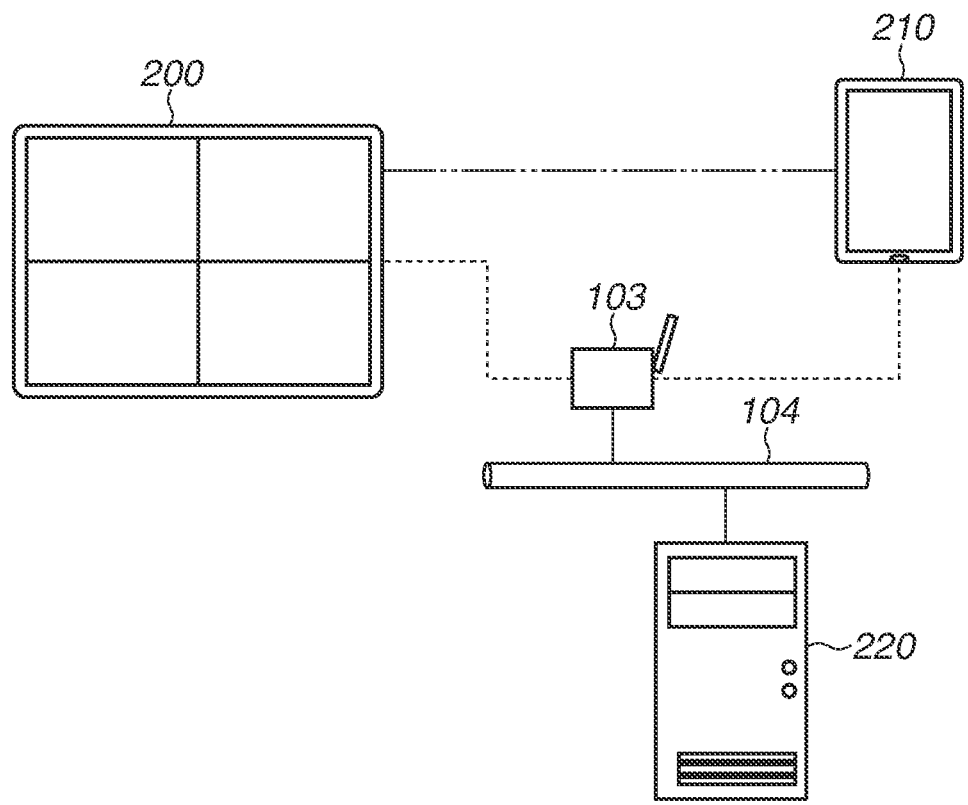
FIG. 1 illustrates a network configuration according to a first exemplary embodiment.

FIG. 1 illustrates an example of the configuration of a radiographing system according to the present exemplary embodiment. As illustrated in FIG. 1, the radiographing system includes a radiographing apparatus 200, a mobile information terminal 210, and a management server 220, all of which are connected to each other by a first communication method via an access point 103 and a local area network (LAN) 104. The radiographing apparatus 200 detects radiations to generate radiographic images.

The radiographing apparatus 200 and the mobile information terminal 210 each include an interface for communicating with each other by a second communication method without passing through the access point 103 and the LAN 104 and can communicate with each other. Examples of the second communication method between the radiographing apparatus 200 and the mobile information terminal 210 include Bluetooth® as a representative standard. Any publicly-known communication method by which the radiographing apparatus 200 and the mobile information terminal 210 can directly or indirectly communicate with each other is applicable.

Figure 2:
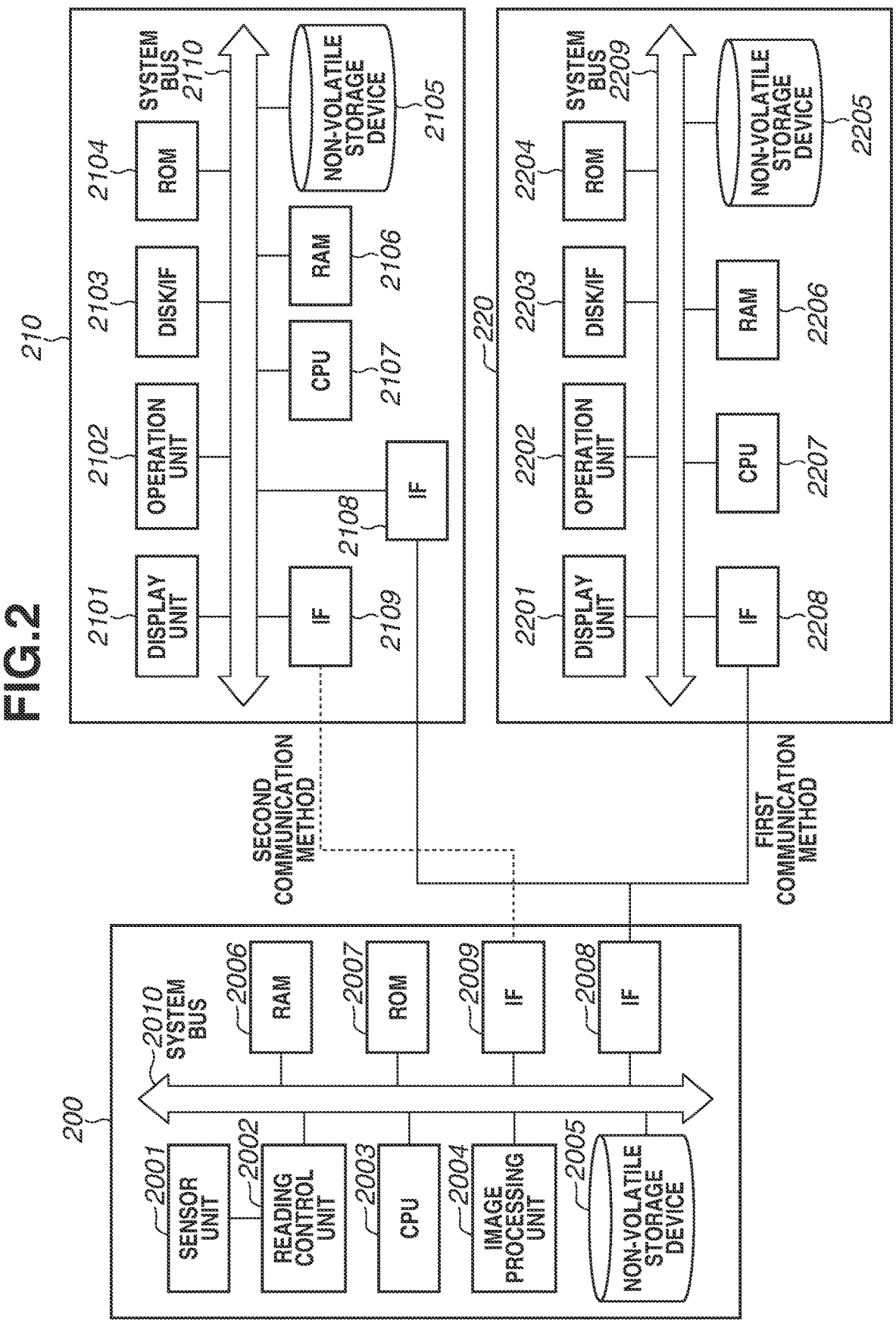
FIG. 2 illustrates a hardware configuration according to the first exemplary embodiment.

Next, an example of the hardware configuration of the radiographing system will be described below with reference to FIG. 2. The radiographing apparatus 200 according to the present exemplary embodiment includes a sensor unit 2001, a reading control unit 2002, a central processing unit (CPU) 2003, an image processing unit 2004, a non-volatile storage device 2005, a random-access memory (RAM) 2006, a read-only memory (ROM) 2007, an interface (IF) (first communication unit) 2008, and an IF (second communication unit) 2009, all of which are connected to each other via a system bus 2010.

The sensor unit 2001 detects radiations transmitted through a subject (not illustrated) and converts the detected radiations into electric signals. The reading control unit 2002 reads the converted electric signals and stores the read electric signals as image data in the RAM 2006 or the non-volatile storage device 2005, such as a hard disk. The CPU 2003 controls a series of processing performed by the radiographing apparatus 200, such as radiographing processing and image transfer processing. The image processing unit 2004 processes image data, including radiographic image data correction processing. The ROM 2007 stores read-only programs, etc.

The IF (first communication unit) 2008 is an interface for communicating with the mobile information terminal 210 and the management server 220. In general, the IF 2008 is realized by a communication interface such as an Ethernet interface or wireless LAN interface. The IF (first communication unit) 2008 can communicate with the mobile information terminal (communication device) 210 by the first communication method (Ethernet, wireless LAN, etc.).

The IF 2008 communicates with the mobile information terminal 210 in a state in which the IF 2008 can communicate with a plurality of communication devices. The IF 2008 communicates with the mobile information terminal 210 via the access point 103. Image data radiographed by the radiographing apparatus 200 is transferred to the management server 220 via the IF 2008.

The IF (second communication unit) 2009 is an interface for directly communicating with the mobile information terminal 210. The IF 2009 is realized by a communication interface such as a Bluetooth® interface and is mainly used to control the radiographing of the radiographing apparatus 200 from the mobile information terminal 210. The IF (second communication unit) 2009 can communicate with the mobile information terminal (communication device) 210 by the second communication method (Bluetooth®, infrared communication, etc.).

The IF 2009 performs exclusive communication with the mobile information terminal 210. The IF 2009 performs communication with the mobile information terminal 210 by the second communication method, which is shorter in communication distance than the first communication method. The IF 2009 performs direct communication with the mobile information terminal 210 without an access point.

The mobile information terminal 210 is a device generally referred to as a tablet or smartphone. The mobile information terminal 210 includes a display unit 2101, an operation unit 2102, a DISK/IF 2103, a ROM 2104, a non-volatile storage device 2105, a RAM 2106, a CPU 2107, an IF (first communication unit) 2108, and an IF (second communication unit) 2109, all of which are connected to each other via a system bus 2110 to form a commonly-used computer configuration.

According to the present exemplary embodiment, the display unit 2101 and the operation unit 2102 are realized by a liquid crystal touch panel that includes a data display function and an input operation reception function. Alternatively, any other technique that includes the data display function and the input operation reception function is applicable. The IF (first communication unit) 2108 is an interface for communicating with the IF 2008 of the radiographing apparatus 200 and is realized by a communication interface such as an Ethernet interface or wireless LAN interface. The IF (second communication unit) 2109 is an interface for communicating with the IF 2009 of the radiographing apparatus 200 and is desirably realized using a communication standard such as Bluetooth®.

The management server 220 is an information processing device such as a workstation or personal computer (PC). The management server 220 includes a display unit 2201, an operation unit 2202, a DISK/IF 2203, a ROM 2204, a non-volatile storage device 2205, a RAM 2206, a CPU 2207, and an IF (first communication unit) 2208, all of which are electrically connected to each other via a system bus 2209 to form a commonly-used computer configuration. The management server (management apparatus) 220 can communicate with the radiographing apparatus 200 and the mobile information terminal 210 by the first communication method.

The IF (first communication unit) 2208 is a communication interface that communicates with the radiographing apparatus 200 and the mobile information terminal 210. In general, the IF 2208 is desirably realized using a communication standard such as Ethernet or wireless LAN.

The display unit 2201 does not have to be an integrated device and can be an external liquid crystal monitor, etc. The operation unit 2202 can be an operation unit in which a display unit and an input unit are integrated together, such as a touch panel. Alternatively, the operation unit 2202 can be an independent device, such as a mouse or keyboard. Alternatively, any other technique that enables input operations on the management server 220 is applicable.

Next, the functional configuration of the radiographing system according to the present exemplary embodiment will be described below with reference to FIG. 3. To simplify the description, only the functional configuration involved in the pairing of the radiographing apparatus 200 and the mobile information terminal 210 will be described, and description of the functional configuration involved in general radiographing, such as radiographic image capturing, image data acquisition, and displaying, is omitted.

Figure 3:
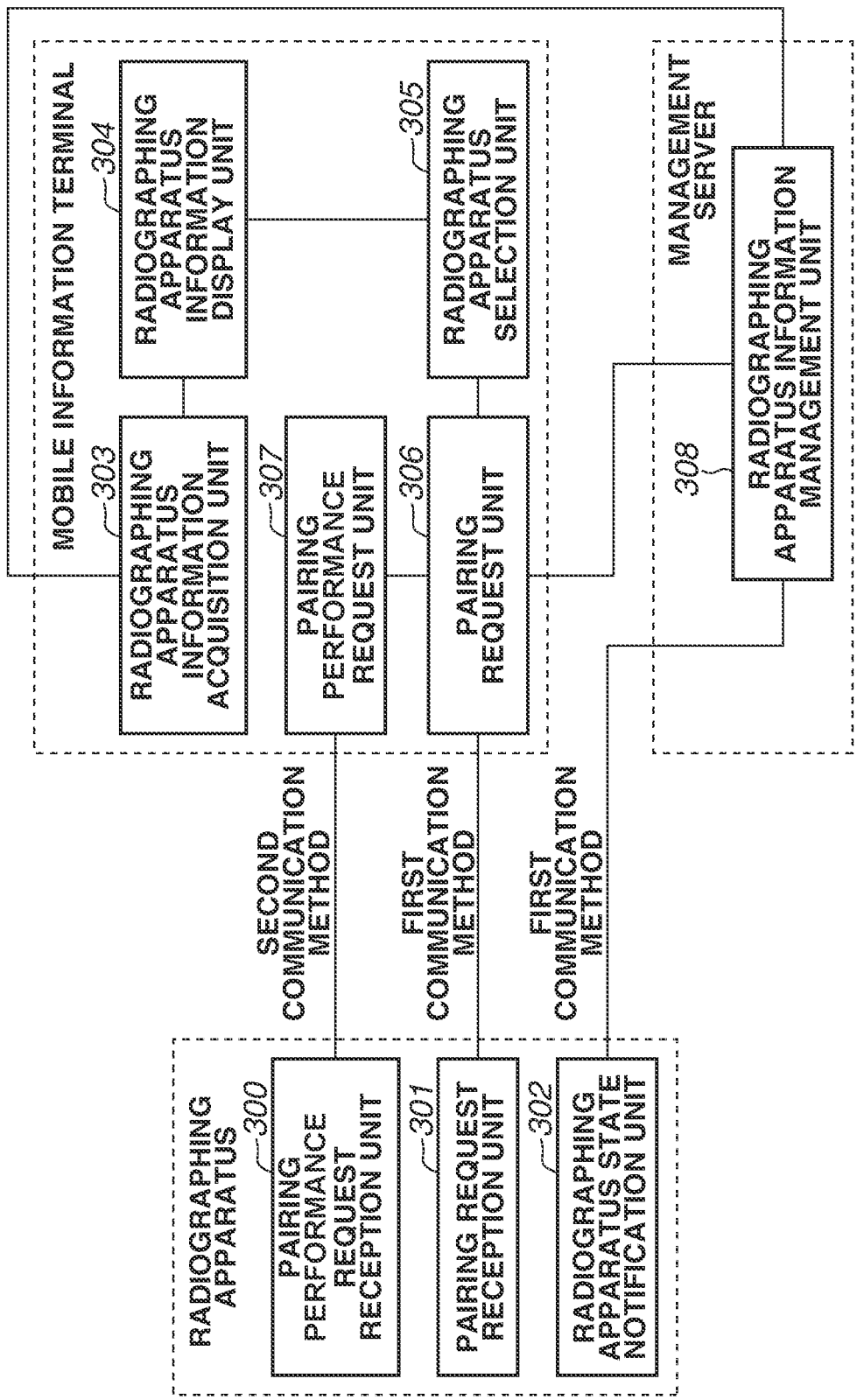
FIG. 3 illustrates a functional configuration according to the first exemplary embodiment.

FIG. 3 is a block diagram illustrating an example of the functional configuration according to the present exemplary embodiment. As illustrated in FIG. 3, the radiographing apparatus 200 includes a pairing performance request reception unit 300, a pairing request reception unit 301, and a radiographing apparatus state notification unit 302. The mobile information terminal 210 includes a radiographing apparatus information acquisition unit 303, a radiographing apparatus information display unit 304, a radiographing apparatus selection unit 305, a pairing request unit 306, and a pairing performance request unit 307. The management server 220 includes a pairing request transfer unit and a radiographing apparatus information management unit 308.

The radiographing apparatus information management unit 308 manages radiographing apparatus information about the radiographing apparatus 200. The radiographing apparatus information management unit 308 stores in the non-volatile storage device 2205 the radiographing apparatus information about the radiographing apparatus 200, such as identification information, sensor size, communication state, pairing state, battery state, power supply state, user information, operational state, reservation information, and function information, and manages the radiographing apparatus information.

The identification information is information for identifying the radiographing apparatus 200. The sensor size information is information about the sensor size of the radiographing apparatus 200. The communication state (first communication information) is information about the communication state of the radiographing apparatus 200 operating in the first communication method. The pairing state (second communication information) is information about the communication state of the radiographing apparatus 200 operating in the second communication method. The battery state (battery information) is information about the battery of the radiographing apparatus 200. The power supply state (power supply information) is information about the power supply state of the radiographing apparatus 200.

The user information is information about the user of the radiographing apparatus 200. The operational state (operational information) is information about the operational state of the radiographing apparatus 200. The reservation information is information about a reservation for the use of the radiographing apparatus 200. The function information is information about the functions of the radiographing apparatus 200. The radiographing apparatus information management unit 308 stores in the non-volatile storage device 2205 examination area information about an area to be radiographed by the radiographing apparatus 200, and manages the examination area information.

The management server 220 transmits to the mobile information terminal 210 one or more of the identification information, the sensor size information, the first communication information, the second communication information, the battery information, the power supply information, the user information, the operational information, the reservation information, the function information, and the examination area information as the radiographing apparatus information about the radiographing apparatus 200.

The radiographing apparatus information is either input before the use of the radiographing system or dynamically changed based on the driving state of the radiographing system during the use of the radiographing system.

The radiographing apparatus information acquisition unit 303 acquires the radiographing apparatus information managed by the radiographing apparatus information management unit 308. The management server (management apparatus) 220 transmits to the mobile information terminal 210 information (radiographing apparatus information) about a radiographing apparatus (or radiographing apparatuses) that communicates with the mobile information terminal 210 by the first communication method. The radiographing apparatus information acquisition unit 303 acquires the radiographing apparatus information from the management server 220 through communication between the IF 2108 of the mobile information terminal 210 and the IF 2208 of the management server 220.

The radiographing apparatus information display unit 304 displays on the display unit 2101 the radiographing apparatus information acquired by the radiographing apparatus information acquisition unit 303.

The radiographing apparatus selection unit 305 selects a radiographing apparatus 200 to be used in radiographing from the radiographing apparatus information displayed by the radiographing apparatus information display unit 304. The selection of a radiographing apparatus 200 is realized by an operation such as a touch on an icon of a radiographing apparatus (sensor) displayed on the touch panel. In this way, the mobile information terminal 210 selects a radiographing apparatus 200 that communicates with the mobile information terminal 210 via the wireless LAN (first communication method). The mobile information terminal 210 selects a radiographing apparatus 200 based on the radiographing apparatus information.

The pairing request unit 306 transmits a pairing request signal (communication request signal) to the radiographing apparatus 200 selected by the radiographing apparatus selection unit 305. The transmitted pairing request signal is transmitted to the pairing request reception unit 301 via the IFs 2108 and 2008.

The mobile information terminal 210 transmits the pairing request signal (communication request signal) to the IF (first communication unit) 2008 of the selected radiographing apparatus 200. The IF (first communication unit) 2008 receives the pairing request signal (communication request signal) for requesting communication with the mobile information terminal (communication device) 210 by the second communication method such as Bluetooth®.

Before transmitting the pairing request signal to the radiographing apparatus 200, the pairing request unit 306 notifies the radiographing apparatus information management unit 308 that the pairing request unit 306 is requesting pairing. This enables the radiographing apparatus information management unit 308 to recognize that the target radiographing apparatus 200 is in the pairing stand-by state. Thus, when a request for information about radiographing apparatuses that are available for use (e.g., a list of radiographing apparatuses that are available for use) is received from another mobile information terminal, information about the radiographing apparatus 200 that is in the pairing stand-by state is not returned to avoid duplication of pairing requests.

The radiographing apparatus 200 having received the pairing request signal shifts the radiographing apparatus 200 to the pairing stand-by state and notifies the pairing request unit 306 that the pairing request is received. When the mobile information terminal 210 detects that the radiographing apparatus 200 is shifted to the pairing stand-by state (stand-by state), the pairing performance request unit 307 transmits a pairing performance request signal (communication performance signal) to the radiographing apparatus 200.

The mobile information terminal 210 transmits to the IF (second communication unit) 2009 of the selected radiographing apparatus 200 the pairing performance request signal (communication performance signal) for performing communication by the second communication method. The IF (second communication unit) 2009 receives from the mobile information terminal (communication device) 210 having received a stand-by state signal the pairing performance request signal (communication performance signal) for performing communication by the second communication method.

The pairing performance request reception unit 300 receives the pairing performance request signal transmitted from the pairing performance request unit 307. The pairing performance request reception unit 300 and the pairing performance request unit 307 communicate with each other via the IF 2009 of the radiographing apparatus 200 and the IF 2109 of the mobile information terminal 210.

The IF (second communication unit) 2009 performs communication with the mobile information terminal (communication device) 210 by the second communication method, such as Bluetooth®, based on the pairing request signal (communication request signal). The mobile information terminal 210 transmits the pairing performance request signal (communication performance signal) to the radiographing apparatus 200 to perform communication with the radiographing apparatus 200 by the second communication method. When the communication is eventually performed, the pairing is completed.

When the pairing is completed, the radiographing apparatus 200 transmits from the radiographing apparatus state notification unit 302 to the radiographing apparatus information management unit 308 a notification that the radiographing apparatus 200 and the mobile information terminal 210 are shifted to a paired state. The radiographing apparatus information management unit 308 updates the state information about the radiographing apparatus 200 managed by the radiographing apparatus information management unit 308 to the paired state based on the paired state information.

Figure 4:
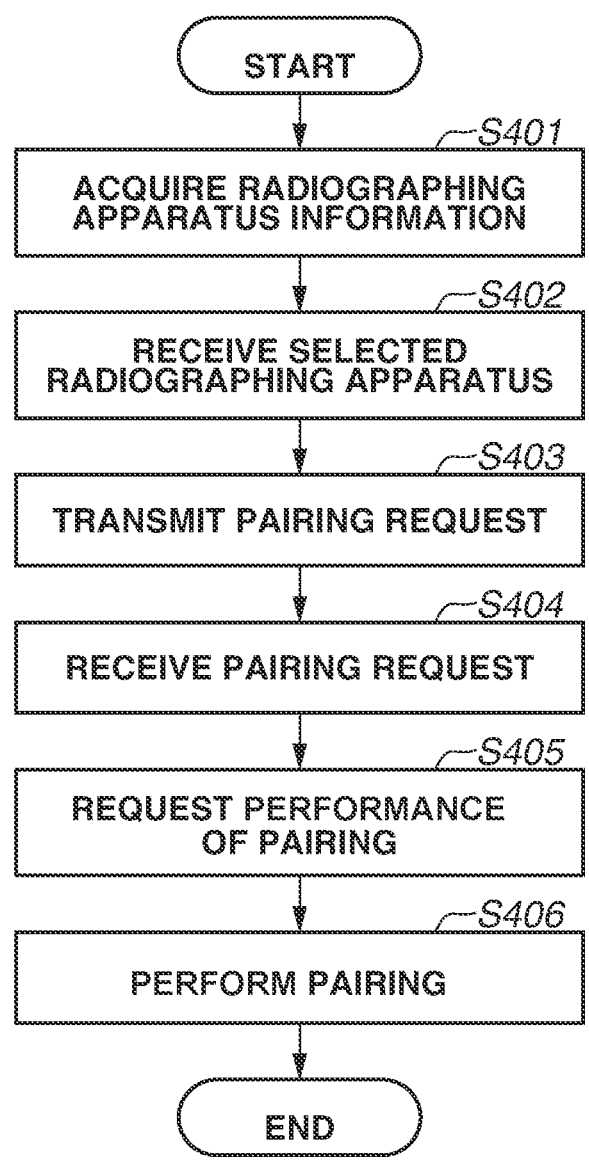
FIG. 4 is a flow chart according to the first exemplary embodiment.

Next, a process of pairing the radiographing apparatus 200 and the mobile information terminal 210 will be described below with reference to FIG. 4. FIG. 4 is a flow chart illustrating the process of pairing the radiographing apparatus 200 and the mobile information terminal 210 in the radiographing system according to the present exemplary embodiment.

In step S401, which is the step of acquiring radiographing apparatus information, the radiographing apparatus information acquisition unit 303 acquires radiographing apparatus information from the management server 220. The radiographing apparatus information display unit 304 displays the radiographing apparatus information on the touch panel, etc. on the mobile information terminal 210. For example, after a round imaging order is received, a candidate radiographing apparatus for use in the round imaging is displayed on a screen of the mobile information terminal 210.

When the radiographing system is used, at this time point, an operator carrying the mobile information terminal 210 is expected to be moving near the storage location of the radiographing apparatus in order to place on a cart a radiographing apparatus that is used in the radiographing.

Step S402 is the step of prompting the operator to select a radiographing apparatus 200 to be used in the radiographing from the radiographing apparatuses 200 displayed on the mobile information terminal 210. Step S402 is executed by the radiographing apparatus selection unit 305.

When the operator, for example, clicks on an icon of a radiographing apparatus 200 displayed on the monitor of the mobile information terminal 210 and the radiographing apparatus selection unit 305 selects the radiographing apparatus 200, the processing proceeds to next step S403. In step S403, a pairing request is transmitted to the selected radiographing apparatus 200. More specifically, in step S403, the pairing request unit 306 of the mobile information terminal 210 transmits the pairing request to the selected radiographing apparatus 200.

Step S404 is the step in which the pairing request reception unit 301 receives a pairing request signal from the mobile information terminal 210 to shift to the pairing stand-by state. A notification that the radiographing apparatus 200 has shifted to the pairing stand-by state is transmitted through a reverse path to the mobile information terminal 210. After receiving the pairing request signal (communication request signal), the IF (first communication unit) 2008 transmits to the mobile information terminal 210 the stand-by state signal indicating that the radiographing apparatus 200 is in the stand-by state in which the radiographing apparatus 200 is waiting for communication with the mobile information terminal (communication device) 210 by the second communication method such as Bluetooth®.

Step S405 is the step of transmitting a request for performance of pairing from the mobile information terminal 210 to the radiographing apparatus 200. If the mobile information terminal 210 detects in step S404 that the radiographing apparatus 200 has shifted to the pairing stand-by state, the pairing performance request unit 307 transmits a pairing performance request signal (communication performance signal) to the radiographing apparatus 200. The IF (second communication unit) 2009 receives the communication performance signal for performing communication by the second communication method from the mobile information terminal (communication device) 210 which has received the stand-by state signal, to perform communication with the mobile information terminal 210 by the second communication method.

Step S406 is the step in which the pairing performance request reception unit 300 of the radiographing apparatus 200 receives the pairing performance request signal from the mobile information terminal 210 to perform pairing.

As a result of the above-described operations, a communication connection between the mobile information terminal 210 and the radiographing apparatus 200 is performed and the mobile information terminal 210 and the radiographing apparatus 200 are able to perform various types of control with respect to the radiographing. Where a plurality of radiographing apparatuses 200 is installed in the same location, it is desirable that a radiographing apparatus 200 with which the paring is performed can be easily identified to recognize the radiographing apparatus 200 that is paired.

For example, an indicator of the radiographing apparatus 200 with which the pairing is performed can blink or light up in specific color to indicate that the pairing with the radiographing apparatus 200 is performed. Alternatively, the radiographing apparatus 200 with which the pairing is performed can generate a sound effect. Alternatively, the indicator of the radiographing apparatus 200 that is a pairing target can be configured to light up in response to an instruction input by a GUI operation on the mobile information terminal 210. Any method can be used as long as the operator can easily recognize that the paring with the mobile information terminal 210 is performed.

Next, examples of the GUI of the mobile information terminal 210 at the time of the pairing of the mobile information terminal 210 and the radiographing apparatus 200 in the radiographing system will be described, with reference to FIGS. 5A to 5C. FIG. 5A illustrates a screen 500, which is an example of the GUI displayed on the mobile information terminal 210. The GUI is a screen that is displayed immediately after an examination order of radiographing is determined before starting the round imaging.

A display area 501 is an examination information display area where the examination order (examination information) received from a radiography information system (RIS), and the examination order reception number, patient ID, patient name, details of radiographing (examination area), etc. are displayed. In the example, an examination "reception number: 99999, patient ID: 12345, patient name: John Doe, and examination area: chest, standing position, front and side" are shown.

While the example in which the above-described four items are specified is described in the present exemplary embodiment, patient information, such as birth date and sex, details of a radiographing procedure, etc. can be displayed. A display area 502 is a radiographing apparatus list display area where a radiographing apparatus information list is displayed by the radiographing apparatus information display unit 304. The information list is acquired from the radiographing apparatus information management unit 308 of the management server 220. In FIG. 5A, three radiographing apparatuses are displayed as the information list.

A display area 503 is a radiographing apparatus icon display area, and the outer shape and state of each radiographing apparatus (sensor) are displayed in the form of an icon. The display area 503 is a GUI including an input function of selecting a radiographing apparatus.

A display area 504 is a radiographing apparatus information display area that displays the name of the radiographing apparatus (sensor), which is C01, the sensor size of the radiographing apparatus, which is 14 inches×17 inches, and a message indicating the radiographing apparatus is available for use. Selection of an icon of a radiographing apparatus results in an instruction to pair with the selected radiographing apparatus, and step S403 is executed to transmit a pairing request to the selected radiographing apparatus.

FIG. 5B illustrates the state of the screen 500 while the pairing request is proceeding. When the radiographing apparatus 200 has shifted to a pairing request reception state (stand-by state), the mobile information terminal 210 executes processing to perform the pairing through the pairing performance request unit 307. After receiving a pairing request signal (communication request signal), the IF (first communication unit) 2008 transmits a stand-by state signal to the mobile information terminal 210.

The display area 503 displays an icon indicating that a pairing process pairing the mobile information terminal 210 and the radiographing apparatus 200 is in progress. The display area 504 displays a message indicating that the pairing process pairing the mobile information terminal 210 and the radiographing apparatus 200 is in progress.

In the process of performing pairing, if the mobile information terminal 210 and the radiographing apparatus 200 cannot receive communication requests from each other, the pairing cannot be performed. In this case, display areas 503 and 504 display an icon or message, respectively, indicating that the pairing cannot be performed between the mobile information terminal 210 and the radiographing apparatus 200.

FIG. 5C illustrates the state in which the pairing is performed between the mobile information terminal 210 and the radiographing apparatus 200, and the mobile information terminal 210 and the radiographing apparatus 200 can directly communicate with each other. The display area 503 displays an icon indicating that the pairing is performed between the mobile information terminal 210 and the radiographing apparatus 200. The display area 504 displays a message indicating that the pairing is performed between the mobile information terminal 210 and the radiographing apparatus 200.

In conventional pairing, an operation for carrying out the pairing needs to be performed on the radiographing apparatus side. In the radiographing system according to the present exemplary embodiment, the pairing between the mobile information terminal 210 and the radiographing apparatus 200 is performed simply by selecting a radiographing apparatus displayed on the mobile information terminal 210. This improves operability of the radiographing apparatus. In the case where a plurality of radiographing apparatuses is available for use, a candidate radiographing apparatus (or candidate radiographing apparatuses) is displayed on the mobile information terminal 201. This enables determining a suitable radiographing apparatus within a short time, which provides a more efficient radiographing operation.

A second exemplary embodiment will be described below. In the first exemplary embodiment, the radiographing apparatus 200 is in the state in which the radiographing apparatus 200 can receive a pairing request in the pairing between the radiographing apparatus 200 and the mobile information terminal 210. There can be, however, cases in which the portable radiographing apparatus 200 is off and cannot receive pairing requests. In the present exemplary embodiment, a case in which power is not supplied to the radiographing apparatus 200 will be described.

Description of configurations, functions, and operations that are similar to those in the exemplary embodiment described above is omitted, and mainly the differences between the present exemplary embodiment and the first exemplary embodiment will be described. According to the present exemplary embodiment, the management server 220 manages information about whether the radiographing apparatus 200 includes a remote power-on function or whether the radiographing apparatus 200 is on.

FIG. 6 is a flow chart illustrating a process of performing pairing between a radiographing apparatus and a mobile information terminal in a radiographing system according to the present exemplary embodiment.

Step S601 is a step of acquiring radiographing apparatus information. In step S601, the radiographing apparatus information acquisition unit 303 acquires radiographing apparatus information from the management server 220. The radiographing apparatus information display unit 304 displays the radiographing apparatus information on the touch panel of the mobile information terminal 210, etc. For example, after a round imaging order is received, a candidate radiographing apparatus (or candidate radiographing apparatuses) for use in the round imaging is displayed on the screen of the mobile information terminal 210.

Step S602 is a step of prompting the operator to select a radiographing apparatus to be used in the radiographing from the radiographing apparatus (or radiographing apparatuses) displayed on the mobile information terminal 210. Step S602 is executed by the radiographing apparatus selection unit 305.

If the operator, for example, clicks on the icon of the radiographing apparatus 200 displayed on the monitor of the mobile information terminal 210 to select the radiographing apparatus 200, the processing proceeds to step S603. Step S603 is a step of determining whether the radiographing apparatus 200 selected in step S602 is online (online information) based on whether the radiographing apparatus 200 is on or is in a connectable state to a network.

The online information about the radiographing apparatus 200 is managed in the management server 220, therefore, the online information can be included in the radiographing apparatus information acquired in step S601. The mobile information terminal 210 can check the online information by transmitting an inquiry to the management server 220.

If it is determined that the radiographing apparatus 200 is offline because, for example, power is not supplied to the radiographing apparatus 200 (NO in step S603), the processing proceeds to step S604. If it is determined that the radiographing apparatus 200 is online because the radiographing apparatus 200 is on and can communicate (YES in step S603), the processing proceeds to step S607.

Step S604 is a step of checking whether the target radiographing apparatus 200 includes the remote power-on function (remote operation information). The remote operation information is also the radiographing apparatus information managed by the management server 220, therefore, the remote operation information can be included in the radiographing apparatus information acquired in step S601. The mobile information terminal 210 can check the remote operation information by transmitting an inquiry to the management server 220.

In step S604, if it is determined that the target radiographing apparatus 200 includes the remote power-on function (YES in step S604), the processing proceeds to step S605. If it is determined that the target radiographing apparatus 200 does not have the remote power-on function (NO in step S604), the processing proceeds to step S606.

Step S605 is a step of transmitting a power-on request to the radiographing apparatus 200 selected in step S602. The mobile information terminal 210 transmits to the radiographing apparatus 200 to which power is not supplied, a power-on signal (power-on request) for turning on the radiographing apparatus 200 based on the power supply information.

This processing can be performed by directly transmitting the power-on signal from the mobile information terminal 210 to the radiographing apparatus 200 or by transmitting the power-on signal from the mobile information terminal 210 to the radiographing apparatus 200 via the management server 220. As long as the power-on request is transmitted to the radiographing apparatus 200, either the mobile information terminal 210 or the management server 220 can transmit the power-on signal.

As to a remote power-on system, for example, a system can be employed in which remote power-on is realized via a wireless LAN as Wake-on Wireless LAN (WoWLAN).

In step S604, if it is determined that the radiographing apparatus 200 does not include the remote power-on function, then in step S606, a message prompting the operator to manually turn on the radiographing apparatus 200 is displayed on the mobile information terminal 210. Steps S607 to S610 correspond to steps S403 to S406 described above, therefore, description of steps S607 to S610 is omitted.

Figure 7A:
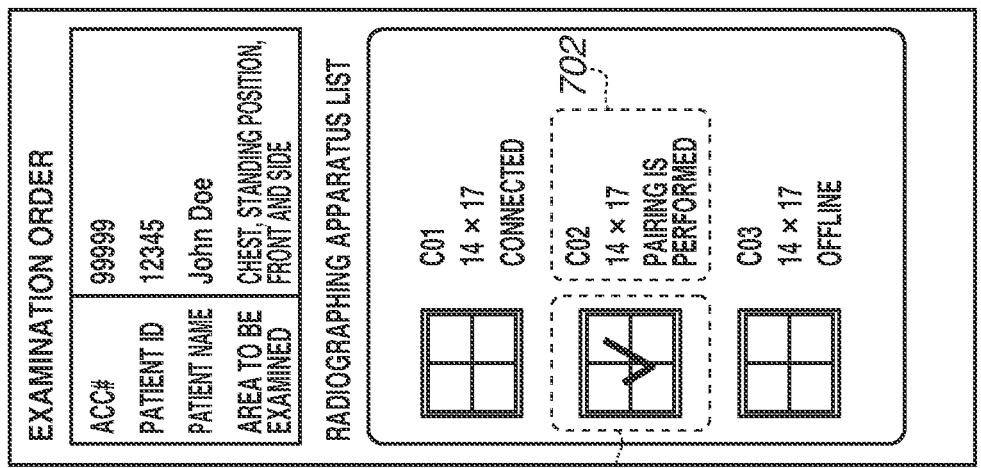
FIGS. 7A, 7B, and 7C illustrate an example of a remote power-on GUI according to the second exemplary embodiment.
Figure 7B:
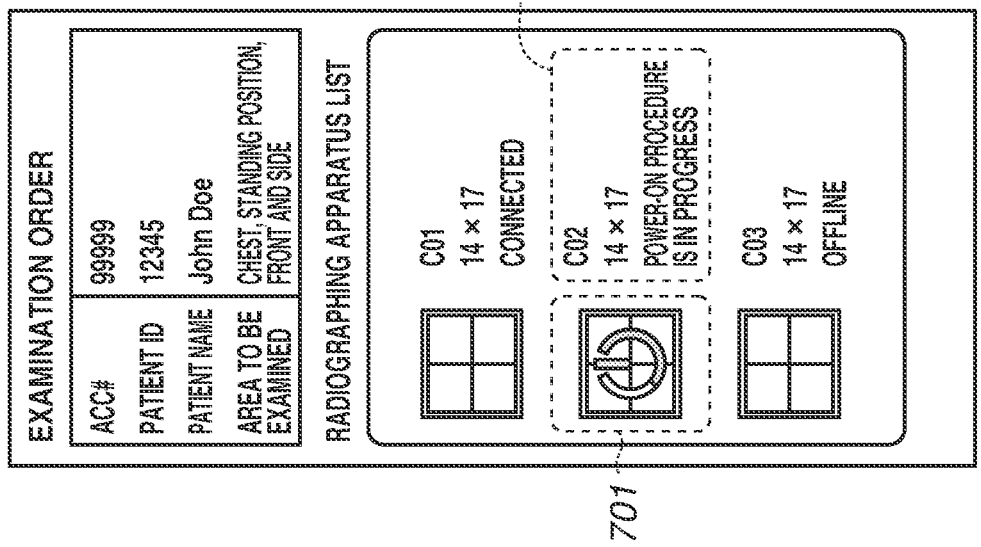
Figure 7C:
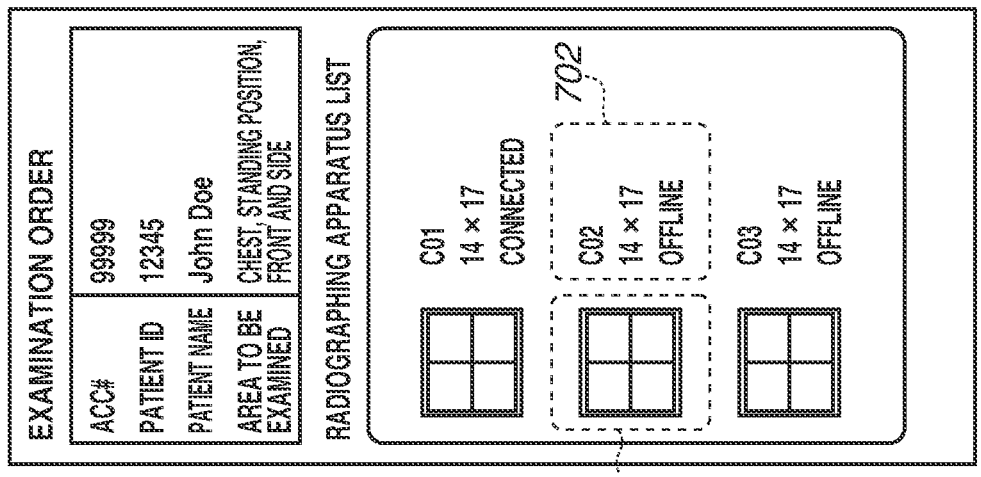

FIGS. 7A to 7C illustrate examples of the GUI displayed on the mobile information terminal 210 in the process of remotely turning on the radiographing apparatus 200 in the case where the radiographing apparatus 200 is not on. In FIG. 7A, a display area 701 is a radiographing apparatus icon display area where the outer shape and state of each radiographing apparatus are displayed in the form of an icon. The display area 701 includes an input GUI function of receiving the selection of a radiographing apparatus.

A display area 702 is a radiographing apparatus information display area that displays the name of the radiographing apparatus (sensor), which is C02, the sensor size of the radiographing apparatus, which is 14 inches×17 inches, and a message indicating the radiographing apparatus is offline.

Selection of an icon of a radiographing apparatus results in an instruction to pair with the selected radiographing apparatus, and steps S603 to S605 are executed to transmit a power-on request to the radiographing apparatus 200. FIG. 7B illustrates the state in which the power-on request is transmitted from the mobile information terminal 210 to the radiographing apparatus 200 in step S605. The display area 701 displays an icon indicating that a power-on procedure is in progress to turn on the radiographing apparatus 200. The display area 702 displays a message indicating that the power-on procedure is in progress to turn on the radiographing apparatus 200.

If the radiographing apparatus 200 having received the power-on request is turned on, steps S607 to S610 are executed to perform pairing between the mobile information terminal 210 and the radiographing apparatus 200, and a screen illustrated in FIG. 7C is displayed. The display area 701 displays an icon indicating that the pairing is performed between the mobile information terminal 210 and the radiographing apparatus 200. The display area 702 displays a message indicating that the pairing is performed between the mobile information terminal 210 and the radiographing apparatus 200.

FIGS. 8A to 8C illustrate examples of the screen displayed in step S606 in the case where the radiographing apparatus 200 selected in step S604 does not include the remote power-on function. In FIG. 8A, a display area 801 is a radiographing apparatus icon display area where the outer shape and state of each radiographing apparatus are displayed in the form of an icon. The display area 801 also includes the input GUI function of selecting a radiographing apparatus.

A display area 802 is a radiographing apparatus information display area that displays the name of the radiographing apparatus (sensor), which is C03, the sensor size of the radiographing apparatus, which is 14 inches×17 inches, and a message indicating the radiographing apparatus is offline.

Selection of an icon of a radiographing apparatus results in an instruction to pair with the selected radiographing apparatus, and steps S603, S604, and S606 are executed in this order, and a screen as illustrated in FIG. 8B is displayed on the mobile information terminal 210. In the case where the radiographing apparatus 200 that does not include the remote power-on function is selected, the mobile information terminal 210 displays a notification to prompt the operator to turn on the radiographing apparatus 200 based on the function information.

A display area 803 is a message display area. In the present case, since the radiographing apparatus 200 does not include the remote power-on function, a message prompting the operator to manually turn on the radiographing apparatus 200 is displayed. The operator, when seeing this message, manually presses a power button of the radiographing apparatus 200 to turn it on.

A display area 804 is an OK button. If the OK button is tapped, the processing proceeds to step S607, which is the step of transmitting a pairing request. Steps S607 to S610 are sequentially executed, and when the pairing is completed, a screen as illustrated in FIG. 8C is displayed. The display area 801 displays an icon indicating that the pairing is performed between the mobile information terminal 210 and the radiographing apparatus 200. The display area 802 displays a message indicating that the pairing is performed between the mobile information terminal 210 and the radiographing apparatus 200.

A display area 805 is a cancel button. If the cancel button is tapped, the display area 803 is closed to return to the state illustrated in FIG. 8A instead of proceeding to step S607, which is the step of transmitting a pairing request.

As described above, even when the radiographing apparatus 200 is not on and is in the offline state, if the radiographing apparatus 200 includes the remote power-on function, the mobile information terminal 210 can remotely turn on the radiographing apparatus 200.

Even when a radiographing apparatus that does not include the remote power-on function and a radiographing apparatus including the remote power-on function are mixed, since the remote operation information is managed by the management server 220, a power-supply guide can be displayed on the mobile information terminal 210. Thus, at the time of pairing with a desired radiographing apparatus, the power-supply of the radiographing apparatus can easily be checked. Thus, efficient radiographing operation can be achieved especially in locations where round imaging is conducted using a plurality of radiographing apparatuses.

A third exemplary embodiment will be described below. In a method according to the third exemplary embodiment, the mobile information terminal 210 acquires radiographing apparatus information from the management server 220, and the radiographing apparatus information display unit 304 displays a candidate radiographing apparatus (or candidate radiographing apparatuses) suitable for the examination to be conducted.

The mobile information terminal 210 selects as examination information one or more of examination order information for identifying an examination order performed by the radiographing apparatus, subject information for identifying a subject, radiographing procedure information for identifying a radiographing procedure, radiographing area information for identifying an area to be radiographed, radiographing direction information for identifying a radiographing direction, and posture information for identifying the posture of the subject. Then, the mobile information terminal 210, based on specification information associated with the examination information, receives from the management server 220 radiographing apparatus information about the radiographing apparatus corresponding to the specification information FIG. 5A indicates that a requested examination is the radiographing of the patient's chest in the standing position from the front and the sides. In the case of chest radiographing, a radiographing apparatus with the sensor size that is a half-cut size (14 inches×17 inches) is generally used so that the entire lung field area is covered. Thus, according to the present exemplary embodiment, even if radiographing apparatuses of other sensor sizes are registered in the management server 220, the radiographing apparatus of the sensor size suitable for the requested examination indicated in FIG. 5A is selected and displayed.

To realize the processing according to the present exemplary embodiment, the management server 220 of the radiographing system manages a correspondence table that associates radiographing protocols with sensor sizes as illustrated in FIG. 9A. The mobile information terminal 210 acquires examination area information about an examination area to be radiographed (radiographing area information) from the RIS, etc. The mobile information terminal 210 selects the examination area information (radiographing area information) "chest, front and side" as the examination information and transmits the examination information to the management server 220.

The management server 220 identifies a sensor size suitable for "chest, front and side" from the correspondence table stored in the management server 220. In the example illustrated in FIG. 9A, the sensor size "14×17" associated with the examination information "chest, front and side" is identified as identifying information.

If the sensor size is identified, the management server 220 searches for a radiographing apparatus with the sensor size "14×17" from the radiographing apparatus information (FIG. 9B) managed by the management server 220. In FIG. 9B, the radiographing apparatuses (named C01, C02, C03, and C06) satisfying the above-described condition are extracted as radiographing apparatuses that are available for use (displayed candidates), and radiographing apparatus information about each of the extracted radiographing apparatuses is transmitted to the mobile information terminal 210.

As illustrated in FIG. 9B, pairing information indicating a mobile information terminal with which a radiographing apparatus is paired is managed, so that radiographing apparatuses already paired can be identified and excluded from the candidates displayed on the radiographing apparatus information display unit 304.

In FIG. 9B, the radiographing apparatus of the name C06 is already paired with Tablet 2, so that the radiographing apparatus information about the radiographing apparatuses of the names C01, C02, and C03 is transmitted as candidate radiographing apparatuses that are available to the mobile information terminal 210. As described above, the management server 220 transmits to the mobile information terminal 210 the radiographing apparatus information about the radiographing apparatuses corresponding to the information for identifying the radiographing apparatus information. Then, as illustrated in FIG. 5A, the mobile information terminal 210 displays the candidate radiographing apparatuses suitable for the examination.

In the present exemplary embodiment, as an example, the management server 220 manages the radiographing apparatus information such as the names of the radiographing apparatuses, examination area, sensor size, and pairing state. The mobile information terminal 210 displays the candidate radiographing apparatuses based on the information for identifying the radiographing apparatus information.

Alternatively, the management server 220 can manage other radiographing apparatus information, and the mobile information terminal 210 can display a candidate radiographing apparatus based on the information for identifying the radiographing apparatus information. Examples of other radiographing apparatus information include remote operation information (function information), identification information, communication state, battery state, power supply state, user information, operational state, and reservation information about the radiographing apparatus.

As described above, the management server 220 can manage the radiographing apparatus information about the radiographing apparatuses and the mobile information terminal 210 can display a candidate radiographing apparatus based on the radiographing apparatus information. For example, the management server 220 can manage the battery state of the radiographing apparatuses, and the mobile information terminal 210 can display the radiographing apparatus, where the display shows that the battery state of the radiographing apparatus is greater than or equal to a predetermined remaining amount of charge.

A fourth exemplary embodiment will be described below. In the first exemplary embodiment, the example in which the radiographing apparatus uses two communication methods, i.e., wireless LAN and Bluetooth®, is described. The present exemplary embodiment is also applicable to a case of using one communication method (e.g., wireless LAN). For example, in a case where a radiographing apparatus communicates with a mobile information terminal using only a wireless LAN interface, wireless LAN communication is performed using an in-hospital network. Sometimes sufficient throughput cannot be achieved depending on the network configuration. Thus, the radiographing apparatus and the mobile information terminal are desirably capable of directly communicating with each other.

In general, mobile information terminals do not include a plurality of wireless LAN (first communication method) interfaces, therefore, it is difficult for a mobile information terminal to directly communicate with a radiographing apparatus while communicating with a management server via the in-hospital network.

In the present exemplary embodiment, even a radiographing apparatus including only one communication interface can perform pairing (direct communication) with a mobile information terminal without decreasing radiographing throughput.

Figure 10A:
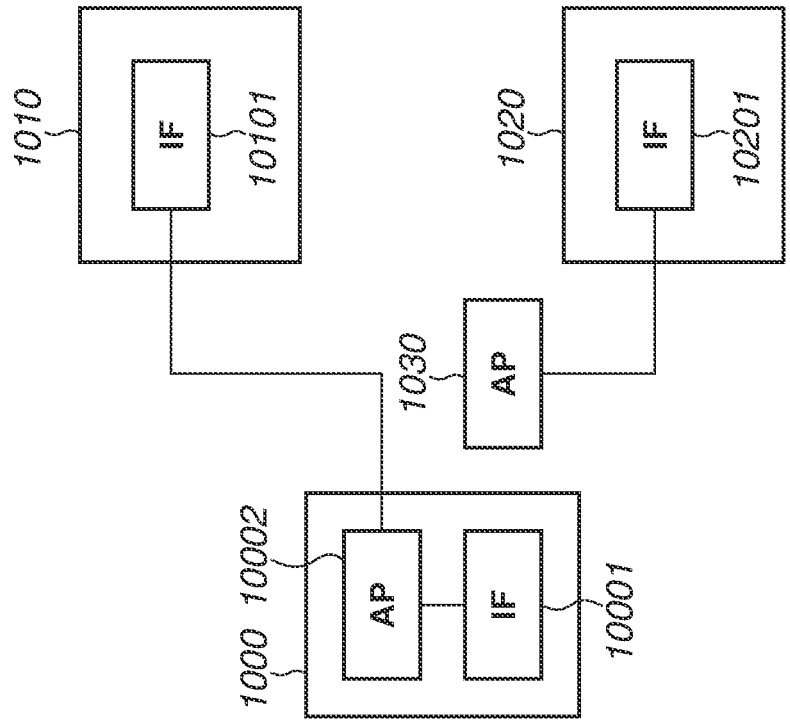
FIG. 10A schematically illustrates a hardware configuration for communication via a first access point according to a fourth exemplary embodiment.
Figure 10B:
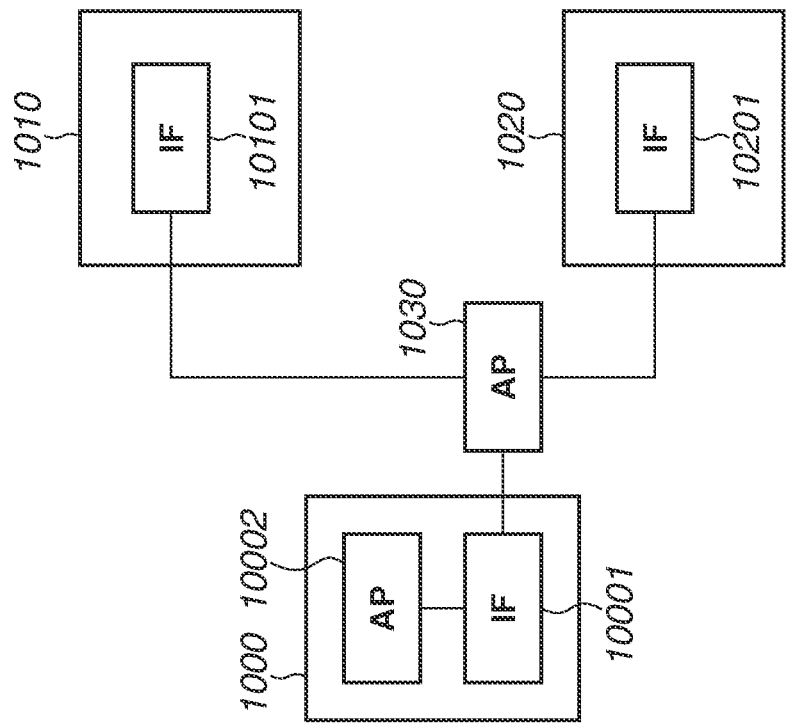
FIG. 10B schematically illustrates a hardware configuration for communication via a second access point according to the fourth exemplary embodiment.

FIGS. 10A and 10B schematically illustrate a hardware configuration according to the present exemplary embodiment. In FIGS. 10A and 10B, the hardware configuration is illustrated in which communication interface portions different from the hardware configuration illustrated in FIG. 2 are highlighted. Portions other than the communication interface portions are similar to those illustrated in FIG. 2. FIG. 10A schematically illustrates a communication state before a mobile information terminal and a radiographing apparatus are paired. FIG. 10B schematically illustrates a communication state in which the mobile information terminal and the radiographing apparatus are paired.

A radiographing apparatus 1000 in FIG. 10A corresponds to the radiographing apparatus 200. A mobile information terminal 1010 in FIG. 10A corresponds to the mobile information terminal 210. A management server 1020 in FIG. 10A corresponds to the management server 220. The radiographing apparatus 1000 includes an IF 10001 and an access point (AP) 10002.

The IF 10001 is an interface for communicating with the mobile information terminal 1010 and the management server 1020. In general, the IF 10001 is realized by a communication interface used in Ethernet, wireless LAN, etc. The IF (communication unit) 10001 can communicate with the mobile information terminal (communication device) 1010 via the first access point 1030 of the first communication method.

The radiographing apparatus 1000 includes the AP 10002 therein and can operate as an access point. The radiographing apparatus 1000 is different from the radiographing apparatus 200 in FIG. 2 in that the radiographing apparatus 1000 includes a second access point 10002 of the first communication method.

The mobile information terminal 1010 includes an IF 10101 and the management server 1020 includes an IF 10201.

As illustrated in FIG. 10A, before the radiographing apparatus 1000 and the mobile information terminal 1010 are paired, the IF 10001 of the radiographing apparatus 1000 and the IF 10101 of the mobile information terminal 1010 are communicably connected via the AP 1030. At this time, the radiographing apparatus 1000 operates as a slave unit electrically connected to the AP 1030.

Next, the configuration after the radiographing apparatus 1000 and the mobile information terminal 1010 are paired will be described. As illustrated in FIG. 10B, after the radiographing apparatus 1000 and the mobile information terminal 1010 are paired, the radiographing apparatus 1000 enables the AP 10002 of the radiographing apparatus 1000 and operates as an access point.

The communication counterpart for the IF 10101 of the mobile information terminal 1010 then switches from the AP 1030 to the AP 10002 of the radiographing apparatus 1000 and the mobile information terminal 1010 and radiographing apparatus 1000 begin to directly communicate with each other. At this time, the mobile information terminal 1010 and the management server 1020 are substantially in a disconnected state, and no communication is performed between the mobile information terminal 1010 and the management server 1020.

Next, a process will be described in which the radiographing apparatus 1000 and the mobile information terminal 1010 communicate with each other using the AP 10002 of the radiographing apparatus 1000 with reference to FIG. 11. FIG. 11 illustrates a process of pairing the radiographing apparatus 1000 including one communication IF and the mobile information terminal 1010 as illustrated in FIGS. 10A and 10B.

Steps S1101 and S1102 are similar to steps S401 and S402 in the first exemplary embodiment, therefore, description of steps S1101 and S1102 is omitted. Step S1103 is a step of transmitting a request to enable the access point (AP) 10002 of the radiographing apparatus 1000 selected in step S1102 to drive the radiographing apparatus 1000 having the AP 10002 in a master unit mode.

The mobile information terminal 1010 transmits to the radiographing apparatus 1000 a communication mode change request (switch signal) to switch from the first access point 1030 to the second access point 10002. The IF (communication unit) 10001 receives the communication mode change request (switch signal) to switch from the first access point 1030 to the second access point 10002. When the communication mode change request (switch signal) is received, the radiographing apparatus 1000 drives the AP 10002 of the radiographing apparatus 1000 serving as a master unit.

Step S1104 is a step in which the mobile information terminal 1010 switches communication between access points, e.g., from an in-hospital access point (AP 1030 to the second access point (AP 10002) of the radiographing apparatus 1000. Step S1105 is a step in which the mobile information terminal 1010 requests the radiographing apparatus 1000 to perform a connection. Step S1105 corresponds to, for example, an association request in wireless LAN communication. Step S1106 is a step enabling association in response to the association request from the mobile information terminal 1010 to perform communication.

As described above, the IF (communication unit) 10001 receives the communication mode change request (switch signal) to switch from the first access point 1030 to the second access point 10002. Thereafter, the IF (communication unit) 10001 performs communication with the mobile information terminal (communication device) 1010 via the second access point 10002.

The radiographing apparatus 1000 transmits to the mobile information terminal 1010 a switching completion signal indicating that switching from the first access point 1030 to the second access point 10002 is completed, and the mobile information terminal 1010 can receive the switching completion signal from the radiographing apparatus 1000.

After the mobile information terminal 1010 and the radiographing apparatus 1000 are able to directly communicate with each other, the mobile information terminal 1010 can perform radiographing control on the radiographing apparatus 1000.

In the case of the present exemplary embodiment, since the communication is switched from the AP 1030 to the AP 10002, image data radiographed by the radiographing apparatus 1000 cannot be transferred from the radiographing apparatus 1000 to the management server 1020. Thus, the radiographing apparatus 1000 is controlled such that the image data is stored in a storage medium and when the radiographing apparatus 1000 becomes capable of communicating with the management server 1020, the radiographing apparatus 1000 transmits the image data to the management server 1020.

Next, a process is described in which after capturing radiographic images is finished, the pairing of the radiographing apparatus 1000 is cancelled and the mobile information terminal 1010 returns to the state illustrated in FIG. 10A. In the radiographing system, if communication is in a state as illustrated in FIG. 10B after the radiographing of radiographic images (image data) is performed, other mobile information terminals cannot be paired with the radiographing apparatus 1000.

To enable the mobile information terminal 1010 to return to the state illustrated in FIG. 10A, the master unit mode of the AP 10002 of the radiographing apparatus 1000 is cancelled at a predetermined timing to make enabling switching the radiographing apparatus 1000 to re-connect as the slave unit of the first access point 1030. The mobile information terminal 1010 stores connection information about the first access point 1030 and transmits to the radiographing apparatus 1000 a switching signal to switch from the second access point 10002 to the first access point 1030. Thereafter, the mobile information terminal 1010 performs communication with the radiographing apparatus 1000 via the first access point 1030 based on the connection information.

Thereafter, the mobile information terminal 1010 performs communication with the radiographing apparatus 1000 via the first access point 1030 based on the connection information. Then, the IF (communication unit) 10001 transmits the image data via the first access point 1030 switched from the second access point 10002.

The timing at which the mobile information terminal 1010 requests (transmits the switch signal to) the radiographing apparatus 1000 to change the communication mode and cancel the master unit mode, is, for example, the timing of completion of radiographic image examination. Alternatively, a button (not illustrated) for switching the communication mode provided on the screen of the mobile information terminal 1010 can be used to switch the access point at a desired timing.

The radiographing apparatus 1000 can automatically cancel the master unit mode and switch the access point if the radiographing apparatus 1000 and the mobile information terminal 1010 have not communicated with each other for a predetermined time or longer.

As described above, pairing of the radiographing apparatus 1000 and the mobile information terminal 1010 occurs even in the case where the radiographing apparatus 1000 does not include a plurality of communication IFs. The radiographing apparatus 1000 and the mobile information terminal 1010 can be paired by enabling the access point (AP) 10002 of the radiographing apparatus 1000 to connect the radiographing apparatus 1000 and the mobile information terminal 1010 to each other such that the radiographing apparatus 1000 and the mobile information terminal 1010 can communicate with each other using the AP 10002.

An exemplary embodiment is also applicable to a case in which a radiographing apparatus is connected to a mobile information terminal such that the radiographing apparatus and the mobile information terminal can communicate directly with each other in a case where a radiographing apparatus includes a plurality of communication interfaces and a radiographing apparatus including one communication interface. Since information about the plurality of radiographing apparatuses is managed by the management server, appropriate pairing is possible by executing a suitable process for each radiographing apparatus based on the number of communication interfaces.

While the present disclosure has been described with reference to exemplary embodiments, it is to be understood that the invention is not limited to the disclosed exemplary embodiments. The invention can be modified or changed within a scope described in claims.

Exemplary embodiments can be executed by supplying software (program) for realizing the functions of the above-described exemplary embodiments to a system or apparatus via a network or various storage mediums and causing a computer (CPU, micro processing unit (MPU), etc.) to read and execute the program. Exemplary embodiments invention can also be realized by a process in which one or more processors of the computer of the system or apparatus read and execute the program, and can also be realized by a circuit (e.g., application specific integrated circuit (ASIC)) which realizes one or more functions.

Other Embodiments

Embodiments can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-203633, filed Oct. 17, 2016, which is hereby incorporated by reference herein in its entirety.

What is claimed is:

1. A radiographing apparatus configured to detect radiation to generate a radiographic image, the radiographing apparatus comprising:
    a first communication unit that wirelessly communicates with a communication device via a first communication method; and
    a second communication unit that wirelessly communicates with the communication device via a second communication method, the second communication method being a method requiring pairing operation,
    wherein the first communication unit receives a communication request signal for shifting to a stand-by state of accepting pairing with the communication device by the second communication method, and wherein the second communication unit receives a communication performance signal transmitted from the communication device having detected the shifting of the radiographing apparatus to the stand-by state in accordance with the communication request signal, and performs pairing and communication with the communication device.

2. The radiographing apparatus according to claim 1, wherein after receiving the communication request signal, the first communication unit transmits to the communication device a stand-by state signal indicating that the radiographing apparatus is in a stand-by state in which the radiographing apparatus is waiting for communication with the communication device via the second communication method, and wherein the second communication unit receives from the communication device that received the stand-by state signal a communication performance signal for performing communication via the second communication method so that communication with the communication device via the second communication method is performed.

3. The radiographing apparatus according to claim 1, wherein the first communication unit communicates with the communication device in a state in which the first communication unit communicates with a plurality of communication devices, and wherein the second communication unit performs communication exclusively with the communication device.

4. The radiographing apparatus according to claim 1, wherein the first communication unit communicates with the communication device via an access point.

5. The radiographing apparatus according to claim 1, wherein the first communication method is a wireless LAN, and the second communication method is Bluetooth.

6. A radiographing system comprising:

a radiographing apparatus configured to detect radiation to generate a radiographic image; and a mobile information terminal configured to communicate with the radiographing apparatus, wherein the radiographing apparatus comprises:

a first communication unit that wirelessly communicates with the mobile information terminal via a first communication method; and a second communication unit that wirelessly communicates with the mobile information terminal via a second communication method, the second communication method being a method requiring pairing operation, wherein the first communication unit receives a communication request signal for shifting to a stand-by state of accepting pairing with the mobile information terminal by the second communication method, and wherein the second communication unit receives a communication performance signal transmitted from the mobile information terminal having detected the shifting of the radiographing apparatus to the stand-by state in accordance with the communication request signal, and performs pairing and communication with the mobile information terminal.

7. The radiographing system according to claim 6, wherein a radiographing apparatus that can communicate with the mobile information terminal via the first communication method is selected at the mobile information terminal, wherein the mobile information terminal transmits the communication request signal to the first communication unit of the selected radiographing apparatus, and wherein the mobile information terminal transmits to the second communication unit of the selected radiographing apparatus a communication performance signal for performing communication via the second communication method so that communication with the radiographing apparatus via the second communication method is performed.

8. The radiographing system according to claim 6, further comprising a management apparatus that communicates with the radiographing apparatus and the mobile information terminal via the first communication method, wherein the management apparatus transmits to the mobile information terminal information about the radiographing apparatus that can communicate with the mobile information terminal via the first communication method.

9. The radiographing system according to claim 8, wherein the management apparatus transmits as radiographing apparatus information about the radiographing apparatus to the mobile information terminal one or more of identification information for identifying the radiographing apparatus, information about a sensor size of the radiographing apparatus, first communication information about a communication state of the radiographing apparatus via the first communication method, second communication information about a communication state of the radiographing apparatus via the second communication method, information about a battery of the radiographing apparatus, power supply information about a power supply state of the radiographing apparatus, information about a user of the radiographing apparatus, information about an operational state of the radiographing apparatus, information about a reservation for use of the radiographing apparatus, information about a function that the radiographing apparatus has, and examination area information about an area to be radiographed by the radiographing apparatus, and wherein the mobile information terminal selects the radiographing apparatus based on the radiographing apparatus information.

10. The radiographing system according to claim 9, wherein the management apparatus transmits to the mobile information terminal the radiographing apparatus information about the radiographing apparatus corresponding to identification information for identifying the radiographing apparatus information.

11. The radiographing system according to claim 10, wherein the mobile information terminal selects as examination information one or more of examination order information for identifying an examination order to be conducted by the radiographing apparatus, subject information for identifying a subject, radiographing procedure information for identifying a radiographing procedure, radiographing area information for identifying an area to be radiographed, radiographing direction information for identifying a radiographing direction, and posture information for identifying a posture of the subject, and wherein the mobile information terminal receives from the management apparatus the information about the radiographing apparatus corresponding to the identification information based on the identification information associated with the examination information.

12. The radiographing system according to claim 9, wherein the mobile information terminal transmits to a radiographing apparatus to which power is not supplied a signal for supplying power to the radiographing apparatus based on the power supply information.

13. The radiographing system according to claim 9, wherein in a case of selecting a radiographing apparatus with no remote power-on function, the mobile information terminal displays an instruction to supply power to the radiographing apparatus based on the function information.

14. The radiographing system according to claim 6, wherein the first communication unit communicates with the mobile information terminal via an access point.

* * * * *